United States Patent [19]
Shindo

[11] Patent Number: 5,755,940
[45] Date of Patent: May 26, 1998

[54] LITHIUM IONIC CONDUCTING GLASS THIN FILM AND CARBON DIOXIDE SENSOR COMPRISING THE GLASS THIN FILM

[75] Inventor: Kiyotaka Shindo, Sodegaura, Japan

[73] Assignee: Mitsui Petrochemical Industries, Ltd., Tokyo, Japan

[21] Appl. No.: 591,650

[22] PCT Filed: Jun. 13, 1995

[86] PCT No.: PCT/JP95/01181

§ 371 Date: Dec. 12, 1996

§ 102(e) Date: Dec. 12, 1996

[87] PCT Pub. No.: WO95/34515

PCT Pub. Date: Dec. 21, 1995

[30] Foreign Application Priority Data

Jun. 13, 1994 [JP] Japan .................................. 6-130294

[51] Int. Cl.⁶ .................................. G01N 27/407
[52] U.S. Cl. .................. 204/424; 204/421; 204/426; 204/427; 205/784
[58] Field of Search ............................. 204/416, 419, 204/420, 421–429; 205/783.5, 784

[56] References Cited

U.S. PATENT DOCUMENTS

| | | | |
|---|---|---|---|
| 1,990,768 | 2/1935 | Youden | 204/420 |
| 2,462,843 | 3/1949 | Cary et al. | 204/420 |
| 2,497,235 | 2/1950 | Perley et al. | 204/420 |
| 2,986,511 | 5/1961 | Digby | 204/420 |
| 3,143,488 | 8/1964 | Arthur . | |
| 3,480,536 | 11/1969 | Arthur . | |
| 3,862,016 | 1/1975 | Arthur et al. | 204/420 |
| 4,502,939 | 3/1985 | Holfelder et al. | 204/426 |
| 5,194,134 | 3/1993 | Futata et al. | 204/416 |
| 5,217,826 | 6/1993 | Yamamura . | |

FOREIGN PATENT DOCUMENTS

| | | |
|---|---|---|
| 3825809 | 10/1960 | Japan . |
| 37-716349 | 10/1962 | Japan . |
| 40-12960 | 6/1965 | Japan . |
| 45-12506 | 7/1970 | Japan . |
| 59-162147 | 9/1984 | Japan . |
| 0495351 | 3/1992 | Japan . |
| 5306117 | 11/1993 | Japan . |
| 5306119 | 11/1993 | Japan . |
| 5310418 | 11/1993 | Japan . |
| 6160347 | 7/1994 | Japan . |
| 6160348 | 7/1994 | Japan . |

OTHER PUBLICATIONS

Imanaka, et al., "Single Surface Sealed Type Carbon Dioxide Gas Sensor Based on a Lithium Ionic Conductor", Denki Kagaki, vol. 61, pp. 909–910, 1993, Month Unavailable.

Mouchon et al., "Sol–Gel Lithium Silicate Electrolyte Thin Films", Mat. Res. Soc. Symp. Proc., vol. 346, 1994 Materials Research, pp. 189–200.

Eisenman et al., "The Glass Electrode", 1965 Month unavailable, pp. 71–86.

*Primary Examiner*—T. Tung
*Attorney, Agent, or Firm*—Sherman and Shalloway

[57] ABSTRACT

The lithium ionic conducting glass thin film of the present invention comprises a glass containing 20 to 80 mol % of an $Li_2O$ component. This glass thin film has a dense structure which shuts off gas and can be used as a solid electrolyte in a carbon dioxide sensor.

The thin carbon dioxide sensor of the present invention comprises the above lithium ionic conducting glass thin film as a solid electrolyte. This sensor enables complete elimination of noise attributed to gas permeation by virtue of the lithium ionic conducting glass thin film having a dense structure with the result that the accuracy of carbon dioxide concentration measurement can be enhanced. Further, the lithium ionic conducting glass is formed into a thin film, so that the sensor has a low internal resistance, acts at low operating temperatures and exhibits a high response speed. Therefore, a heater having a capacity smaller than in the prior art can be used in the sensor, so that, even when a structure integral with a heater and the like is employed, miniaturization of the sensor can be realized.

21 Claims, 4 Drawing Sheets

LITHIUM IONIC CONDUCTING GLASS THIN FILM AND CARBON DIOXIDE SENSOR COMPRISING THE GLASS THIN FILM

TECHNICAL FIELD

The present invention relates to a lithium ionic conducting glass thin film and a carbon dioxide sensor comprising the lithium ionic conducting glass thin film. This carbon dioxide sensor is compact, of the power saving type and inexpensive and can measure the concentration of carbon dioxide in the air.

BACKGROUND ART

The conventional carbon dioxide sensor of the solid electrolyte type comprises a sort of battery in which a noble metal electrode and a metal carbonate capable of creating a dissociation equilibrium with carbon dioxide are arranged on one side of a bulky solid electrolyte composed of a sintered ceramic body capable of conducting alkali ions such as Na+ and Li+ while a noble metal electrode is disposed on the opposite side of the bulky solid electrolyte and in which, when carbon dioxide contacts the metal carbonate, an electromotive force depending on the concentration of carbon dioxide is generated between the two electrodes. This electromotive force satisfies the following Nernst formula:

$$E = E_0 + (RT/nF)\ln(P_{CO_2})$$

wherein $E_0$ is a constant, R is a gas constant, T is an absolute temperature, n is the number of kinetic electrons, F is the Faraday constant and $P_{CO_2}$ is a partial pressure of carbon dioxide. That is, the above carbon dioxide sensor enables determining the concentration of carbon dioxide by measuring the electromotive force.

It has been reported that, when the reference electrode of the conventional carbon dioxide sensor of the solid electrolyte type is composed of an oxygen ionic conductor and a noble metal electrode, the whole body of the carbon dioxide sensor can be inserted in a subject gas in the measurement of carbon dioxide concentration (Nobuhito IMANAKA et al, Denki Kagaku, 61, 909 (1993)).

The carbon dioxide sensor of the solid electrolyte type detects the concentration of carbon dioxide by an electrode reaction effected between the metal carbonate disposed on one side of the solid electrolyte layer and carbon dioxide, so that the metal carbonate side is left open to the subject atmosphere while the opposite side is left open to the reference concentration atmosphere (generally, the air) in the measurement of carbon dioxide concentration. Therefore, the solid electrolyte for use therein is required to have a dense structure which completely shuts off both the atmospheres.

However, the conventionally proposed carbon dioxide sensor of the solid electrolyte type is in the form of a pellet having a thickness ranging from several millimeters to several centimeters and a size ranging from several millimeters square to several centimeters square and prepared by the process such as the melt solidification process or the sintering process. The sintered ceramic body having been employed as the solid electrolyte has a porous structure, so that it occurs that carbon dioxide permeates the sintered ceramic body to thereby cause sensor output variation, i.e., noise. This is the cause of error found in carbon dioxide concentration measurements.

The internal resistance of the carbon dioxide sensor is in direct proportion to the thickness of the employed solid electrolyte. In the use of the bulky solid electrolyte, the large thickness thereof leads to an extremely large internal resistance, so that the electromotive force of the carbon dioxide sensor is lowered to thereby disenable accurate measurement of the carbon dioxide concentration. Thus, for lowering the internal resistance, the carbon dioxide sensor must be used at high temperatures such that the ion conductivity is high and the internal resistance is reduced, so that the operating temperature of the carbon dioxide sensor is generally as very high as about 350° to 600° C. The carbon dioxide sensor must be provided with a heater in the vicinity thereof for achieving the practical use of the carbon dioxide sensor. The heater for use therein must have a large capacity, so that the problem is encountered that the whole body of the carbon dioxide sensor inevitably has a large volume.

Although a thin film of solid electrolyte is especially desired for miniaturizing the whole body of the carbon dioxide sensor, obtaining a thin film is difficult of a sintered body of a ceramic such as β-alumina, NASICON ($Na_{1+x}ZrSi_xP_{3-x}O_{12}$ wherein x is 0–3) or LISICON ($Li_{16-2x}Zn(GeO_4)_4$ wherein x is 0–8) having generally been employed as the solid electrolyte. Even if a thin film of such a sintered ceramic body is managed to obtain, the thin film formed sintered body is polycrystalline, so that there is a problem on the denseness for completely shutting off the gas present between the detector electrode and the reference electrode. When this thin film formed sintered body is used as the solid electrolyte, it occurs that the gas permeation therethrough brings about sensor output variation to thereby result in the cause of error.

The speed of response of the carbon dioxide sensor is governed by the rate of diffusion of carbon dioxide in the metal carbonate employed in the detector electrode. The formation of the metal carbonate into a thin film is needed for increasing the response speed from the conventional about several minutes to several tens of seconds. However, the formation of the metal carbonate into a thin film is difficult in the use of the conventional melt solidification process or sintering process.

Therefore, if a lithium ionic conducting glass thin film and a thin metal carbonate film are developed, its industrial value is striking.

An object of the present invention is to provide a lithium ionic conducting glass thin film having a dense structure which shuts off gases. Another object of the present invention is to provide a compact thin carbon dioxide sensor which is free from noise attributed to gas permeation, exhibits a high response speed at low operating temperatures and is of the power saving type.

DISCLOSURE OF THE INVENTION

The lithium ionic conducting (conductive) glass thin film of the present invention comprises a glass containing 20 to 80 mol % of an $Li_2O$ component.

The thin carbon dioxide sensor of the present invention comprises a lithium ionic conducting (conductive) glass thin film as a solid electrolyte.

It is preferred that the lithium ionic conducting glass thin film for use in the thin carbon dioxide sensor be a thin film comprising a material represented by the formula:

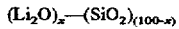

wherein 20 mol % ≧ x mol % ≧ 80 mol %. Especially, it is preferred that the lithium ionic conducting glass thin film be one formed by the sputtering process.

Preferred examples of the thin carbon dioxide sensors according to the present invention include:

(1) a thin carbon dioxide sensor comprises a layer of metal carbonate having a meshed noble metal electrode buried therein, a lithium ionic conducting glass thin film as a solid electrolyte and a layer of noble metal electrode laminated in this sequence;

(2) a thin carbon dioxide sensor wherein a lithium ionic conducting glass thin film and a thin metal carbonate film in this sequence are laminated to one surface of a substrate, preferably, an oxygen ionic conducting ceramic substrate and, further, a thin noble metal electrode film is laminated to the surface of the thin metal carbonate film, and wherein a thin noble metal electrode film and a thin film heater are laminated to the other surface of the substrate in a fashion such that the latter thin noble metal electrode film and the thin film heater are arranged so as not to contact each other;

(3) a thin carbon dioxide sensor wherein a lithium ionic conducting glass thin film and a thin noble metal electrode film in this sequence are laminated to one surface of a substrate, preferably, an oxygen ionic conducting ceramic substrate and, further, a thin metal carbonate film is laminated to the surface of the thin noble metal electrode film, and wherein a thin noble metal electrode film and a thin film heater are laminated to the other surface of the substrate in a fashion such that the latter thin noble metal electrode film and the thin film heater are arranged so as not to contact each other;

(4) a thin carbon dioxide sensor wherein a lithium ionic conducting glass thin film and a thin noble metal electrode film are laminated to one surface of a substrate, preferably, an oxygen ionic conducting ceramic substrate in a fashion such that the lithium ionic conducting glass thin film and the thin noble ionic metal electrode film are arranged so as not to contact each other, a thin metal carbonate film is laminated to the surface of the lithium ionic conducting glass thin film and further a thin noble metal electrode film is laminated to the surface of the thin metal carbonate film, and wherein a thin film heater is laminated to the other surface of the substrate;

(5) a thin carbon dioxide sensor wherein a lithium ionic conducting glass thin film and a thin noble metal electrode film are laminated to one surface of a substrate, preferably, an oxygen ionic conducting ceramic substrate in a fashion such that the lithium ionic conducting glass thin film and the thin noble metal electrode film are arranged so as not to contact each other, a thin noble metal electrode film is laminated to the surface of the lithium ionic conducting glass thin film and further a thin metal carbonate film is laminated to the surface of this thin noble metal electrode film, and wherein a thin film heater is laminated to the other surface of the substrate;

(6) a thin carbon dioxide sensor wherein an oxygen ionic conducting ceramic thin film is laminated to a surface of a plane heater substrate, a lithium ionic conducting glass thin film and a thin noble metal electrode film are laminated to the surface of the oxygen ionic conducting ceramic thin film in a fashion such that the lithium ionic conducting glass thin film and the thin noble metal electrode film are arranged so as not to contact each other, a thin metal carbonate film is laminated to the surface of the lithium ionic conducting glass thin film and further a thin noble metal electrode film is laminated to the surface of the thin metal carbonate film; and (7) a thin carbon dioxide sensor wherein an oxygen ionic conducting ceramic thin film is laminated to a surface of a plane heater substrate, a lithium ionic conducting glass thin film and a thin noble metal electrode film are laminated to the surface of the oxygen ionic conducting ceramic thin film in a fashion such that the lithium ionic conducting glass thin film and the thin noble metal electrode film are arranged so as not to contact each other, a thin noble metal electrode film is laminated to the surface of the lithium ionic conducting glass thin film and further a thin metal carbonate film is laminated to the surface of this thin noble metal electrode film.

BEST MODE FOR CARRYING OUT THE INVENTION

The lithium ionic conducting glass thin film of the present invention and the thin carbon dioxide sensor comprising the glass thin film will now be described in detail.

Lithium ionic conducting class thin film

The lithium ionic conducting glass thin film of the present invention comprises a glass containing 20 to 80 mol % of an $Li_2O$ component and is a solid electrolyte.

Examples of the lithium ionic conducting glass thin films include glass thin films comprising respective materials represented by the formulae:

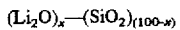

$(Li_2O)_x$—$(SiO_2)_{(100-x)}$ wherein 20 mol % $\geq$ x mol % $\geq$ 80 mol %;

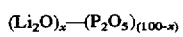

$(Li_2O)_x$—$(P_2O_5)_{(100-x)}$ wherein 30 mol % $\geq$ x mol % $\geq$ 70 mol %;

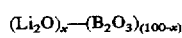

$(Li_2O)_x$—$(B_2O_3)_{(100-x)}$ wherein 30 mol % $\geq$ x mol % $\geq$ 70 mol %; and

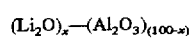

$(Li_2O)_x$—$(Al_2O_3)_{(100-x)}$ wherein 30 mol % ≧ x mol % ≧ 70 mol %.

The above lithium ionic conducting glass thin film can generally be formed by, for example, any of the sputtering, ion plating, ion beam evaporation, CVD, vacuum evaporation, electron beam evaporation, screen printing, spin coating and sol gel processes. Of these, the lithium ionic conducting glass thin film formed by the sputtering process is preferred.

The lithium ionic conducting glass thin film of the present invention is a glass formed by the film forming process such as the sputtering process, so that it has a dense structure and is excellent in capability of shutting off gases. In this connection, Nobuhito IMANAKA et al, Denki Kagaku, 61, 909 (1993) describe a sintered body, as a lithium ionic conductor, prepared from a powder obtained by mixing together $Li_2CO_3$, $TiO_2$, $(NH_4)H_2PO_4$ and $Li3PO4$ in a molar ratio of 0.5:2:3:0.2.

Thin carbon dioxide sensor

The thin carbon dioxide sensor of the present invention will be described below with reference to examples of thin carbon dioxide sensors illustrated in FIGS. 1 to 4.

First, the thin carbon dioxide sensor illustrated in FIG. 1 will be described.

Figure 1:
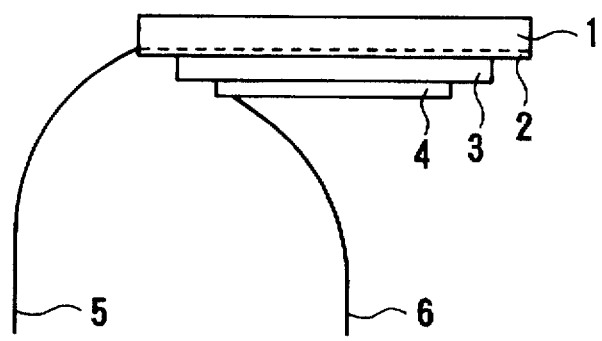
FIGS. 1, 2, 3 and 4 are explanatory diagrams showing examples of the structures of the thin carbon dioxide sensors according to the present invention.

The thin carbon dioxide sensor of FIG. 1 includes a layer of metal carbonate 1 having a meshed noble metal electrode 2 buried therein, a lithium ionic conducting glass thin film 3 as a solid electrolyte and a layer of noble metal electrode 4 laminated in this sequence. The noble metal electrodes 2 and 4 are provided with respective leads 5 and 6 for electromotive force measurement.

In this arrangement, the metal carbonate 1 side is brought into contact with the measured atmosphere while the noble metal electrode 4 side is brought into contact with the reference atmosphere such as the air. The two atmospheres are partitioned from each other.

Examples of the above metal carbonates 1 include lithium carbonate, sodium carbonate, potassium carbonate, barium carbonate, strontium carbonate and calcium carbonate. Of these, lithium carbonate or a mixture of lithium carbonate and another carbonate, especially, barium carbonate or calcium carbonate is preferably used.

The thickness of the layer of the above metal carbonate depends on the type of the metal carbonate but generally ranges from 0.01 to 3 mm and preferably from 0.05 to 1 mm.

The lithium ionic conducting glass thin film 3 for use in this invention is the above lithium ionic conducting glass thin film of the present invention and has a dense structure.

Examples of the lithium ionic conducting glass thin films are as set forth above. Of them, preferred examples are glass thin films composed of respective materials represented by the formula:

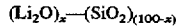

$(Li_2O)_x$—$(SiO_2)_{(100-x)}$ wherein 20 mol % ≧ x mol % ≧ 80 mol %. Especially preferred examples are glass thin films composed of respective materials represented by the above formula in which x ranges from 40 to 60.

For example, $Nb_2O_5$, $Ta_2O_5$ or $WO_3$ may be added to $(Li_2O)_x$—$(SiO_2)_{(100-x)}$ in an amount of preferably 1 to 20 mol % and more preferably 5 to 15 mol % so as to increase the crystallization temperature and the ionic conductivity.

In particular, the lithium ionic conducting glass thin film formed by the sputtering process is preferred.

In the present invention, preferred use is made of a glass thin film of $(Li_2O)_{45}$—$(SiO_2)_{55}$ formed by the sputtering process.

The use of the above lithium ionic conducting glass thin film as the solid electrolyte 3 enables miniaturization of the sensor, so that miniaturization of the whole body of the carbon dioxide sensor together with power saving can be attained by the employment of a heater with a capacity smaller than in the prior art.

The thickness of the above lithium ionic conducting glass thin film generally ranges from 0.5 to 10 μm and preferably from 1 to 5 μm.

Each of the above noble metal electrodes 2 and 4 may be composed of, for example, any of platinum, gold and silver, of which platinum and gold are preferred.

Each of the above leads 5 and 6 may be composed of, for example, any of platinum, gold and silver, of which platinum and gold are preferred.

Now, with respect to the carbon dioxide sensors of FIGS. 2 to 4, the structures thereof will first be described and the description of the constituent materials will follow thereafter.

Figure 2:
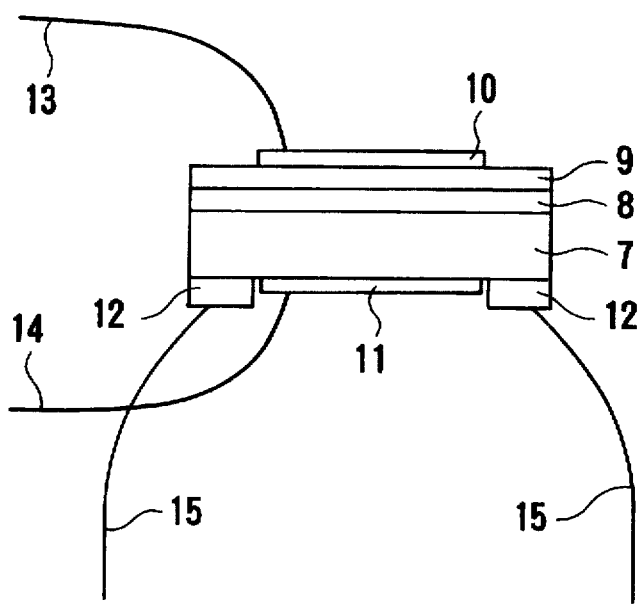

Structure of thin carbon dioxide sensor of FIG. 2

In the thin carbon dioxide sensor of FIG. 2, a lithium ionic conducting glass thin film 8 and a thin metal carbonate film 9 in this sequence are laminated to one surface of an oxygen ionic conducting ceramic substrate 7, preferably, in the entirety of the surface and, further, a thin noble metal electrode film 10 is laminated to part of the surface of the thin metal carbonate film 9.

Furthermore, a thin noble metal electrode film 11 and a thin film heater 12 are laminated to the other surface of the oxygen ionic conducting ceramic substrate 7 in a fashion such that the thin noble metal electrode film 11 and the thin film heater 12 are arranged so as not to contact each other.

The thin noble metal electrode films 10 and 11 are provided with respective leads 13 and 14 for electromotive force measurement. The thin film heater 12 is provided with a heater lead 15.

The thin noble metal electrode film 10 and the thin metal carbonate film 9 structures a detecting electrode. The oxygen Ionic conducting ceramic substrate 7 and the thin noble metal electrode film 11 structures a reference electrode. The thin noble metal electrode film 10 and the thin metal carbonate film 9 structuring a detecting electrode may be laminated in reverse sequence.

Figure 3:
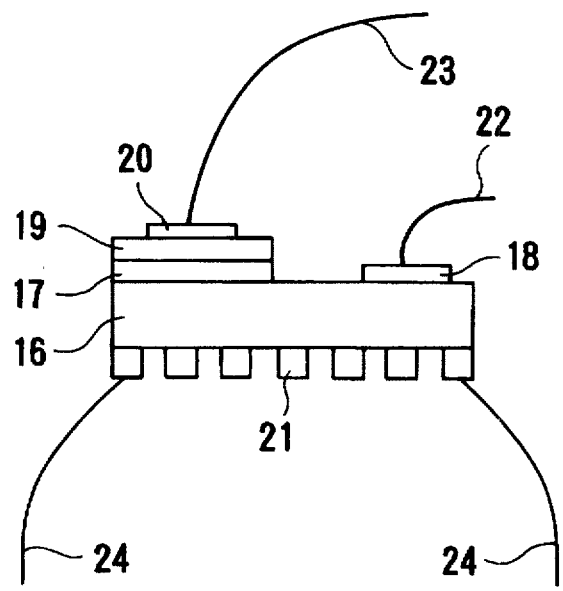

Structure of thin carbon dioxide sensor of FIG. 3

In the thin carbon dioxide sensor of FIG. 3, a lithium ionic conducting glass thin film 17 and a thin noble metal electrode film 18 are laminated to one surface of an oxygen ionic conducting ceramic substrate 16 in a fashion such that the lithium ionic conducting glass thin film 17 and the thin noble metal electrode film 18 are arranged so as not to contact each other, a thin metal carbonate film 19 is laminated to the entire surface of the lithium ionic conducting glass thin film 17 and further a thin noble metal electrode film 20 is laminated to part of the surface of the thin metal carbonate film 19.

Further, a thin film heater 21 is laminated to the other surface of the oxygen ionic conducting ceramic substrate 16.

The thin noble metal electrode films 18 and 20 are provided with respective leads 22 and 23 for electromotive force measurement. The thin film heater 21 is provided with a heater lead 24.

The thin noble metal electrode film 20 and the thin metal carbonate film 19 structures a detector electrode. The oxygen ionic conducting ceramic substrate 16 and the thin noble metal electrode film 18 structures a reference electrode. The thin noble metal electrode film 20 and the thin metal carbonate film 19 structuring a detecting electrode may be laminated in reverse sequence.

Figure 4:
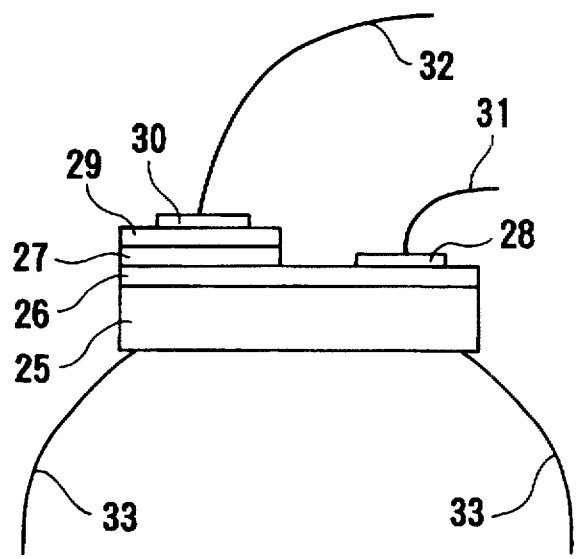

Structure of thin carbon dioxide sensor of FIG. 4

In the thin carbon dioxide sensor of FIG. 4, an oxygen ionic conducting ceramic thin film 26 is laminated to a surface, preferably, the entire surface of a plane heater substrate 25, a lithium ionic conducting glass thin film 27 and a thin noble metal electrode film 28 are laminated to the surface of the oxygen ionic conducting ceramic thin film 26 in a fashion such that the lithium ionic conducting glass thin film 27 and the thin noble metal electrode film 28 are arranged so as not to contact each other, a thin metal carbonate film 29 is laminated to the entire surface of the lithium ionic conducting glass thin film 27 and further a thin noble metal electrode film 30 is laminated to the surface of the thin metal carbonate film 29.

The thin noble metal electrode films 28 and 30 are provided with respective leads 31 and 32 for electromotive force measurement. The thin film heater 25 is provided with a heater lead 33.

The thin noble metal electrode film 30 and the thin metal carbonate film 29 structures a detecting electrode. The oxygen ionic conducting ceramic substrate 26 and the thin noble metal electrode film 28 structures a reference electrode. The thin noble metal electrode film 30 and the thin metal carbonate film 29 structuring a detecting electrode may be laminated in reverse sequence.

Components of thin carbon dioxide sensors of FIGS. 2 to 4

Examples of the oxygen ionic conducting ceramic substrates 7 and 16 of FIGS. 2 and 3 include substrates of zirconia stabilized with any of the oxides $Y_2O_3$, MgO and CaO. The content of each of the oxides $Y_2O_3$, MgO and CaO in the substrate ranges from 5 to 20 mol %.

The thickness of each of the above substrates preferably ranges from 20 μm to 1 mm.

The lithium ionic conducting glass thin films 8, 17 and 27 of FIGS. 2 to 4 are identical with the above lithium ionic conducting glass thin film 3 of FIG. 1.

The thickness of each of the lithium ionic conducting glass thin films preferably ranges from 0.1 to 20 μm and more preferably from 0.5 to 5 μm.

The respective metal carbonates composing the thin metal carbonate films 9, 19 and 29 of FIGS. 2 to 4 are identical with the metal carbonate employed in the layer of metal carbonate 1 of FIG. 1. It is preferably lithium carbonate or a mixture of lithium carbonate and another carbonate.

The above thin metal carbonate film can generally be formed by, for example, any of the sputtering, ion plating, ion beam evaporation, CVD, vacuum beam evaporation, electron beam evaporation, screen printing, spin coating and sol gel processes. Of these, the thin metal carbonate film formed by the sputtering process is preferred.

The thickness of the thin metal carbonate film preferably ranges from 0.1 to 20 μm and more preferably from 0.5 to 5 μm.

A preferred example of the thin noble metal electrode films 10, 11, 18, 20, 28 and 30 of FIGS. 2 to 4 is a thin film of gold or platinum.

The above thin noble metal electrode film can generally be formed by, for example, any of the sputtering, ion plating, ion beam evaporation, CVD, vacuum evaporation, electron beam evaporation, screen printing, spin coating and sol gel processes. Of these, the thin noble metal electrode film formed by the sputtering process is preferred. In this process, a porous thin noble metal electrode film of high gas permeation can be formed by controlling sputtering conditions. This thin noble metal electrode film can be used in combination with a meshed noble metal electrode.

The thickness of the thin noble metal electrode film preferably ranges from 0.1 to 10 μm and more preferably from 0.2 to 2 μm.

Examples of the oxygen ionic conducting ceramic thin film 26 of FIG. 4 include substrates of zirconia stabilized with any of the oxides $Y_2O_3$, MgO and CaO. The content of each of the oxides $Y_2O_3$, MgO and CaO in the substrate ranges from 5 to 20 mol %.

The above oxygen ionic conducting ceramic thin film can generally be formed by, for example, any of the sputtering, ion plating, ion beam evaporation, CVD, vacuum evaporation, electron beam evaporation, screen printing, spin coating and sol gel processes. Of these, the oxygen ionic conducting ceramic thin film formed by the sputtering process is preferred.

The thickness of the oxygen ionic conducting ceramic thin film preferably ranges from 0.1 to 20 μm and still preferably from 0.5 to 5 μm.

Each of the thin film heaters 12 and 21 of FIGS. 2 and 3 is composed of a platinum/rhodium alloy, a platinum/palladium alloy, ruthenium oxide or the like.

The above thin film heater can generally be formed by, for example, any of the sputtering, ion plating, ion beam evaporation, CVD, vacuum evaporation, electron beam evaporation, screen printing, spin coating and sol gel processes. Of these, the thin film heater formed by the sputtering process is preferred.

The thickness of the thin film heater preferably ranges from 0.1 to 10 μm and more preferably from 0.2 to 2 μm. The plane heater substrate 25 of FIG. 4 is composed of a platinum/rhodium alloy, a platinum/palladium alloy, ruthenium oxide or the like.

The thickness of the plane heater substrate preferably ranges from 20 μm to 1 mm.

Effect of the Invention

The lithium ionic conducting glass thin film of the present invention comprises a glass containing 20 to 80 mol % of an $Li_2O$ component, so that it has a dense structure which shuts off gases and can be used as a solid electrolyte of a carbon dioxide sensor.

Further, the lithium ionic conducting glass thin film of the present invention finds applications in a thin lithium secondary-battery (microbattery), an analog memory, an electrochromic element (dimmer glass) and the like.

The solid electrolyte of the thin carbon dioxide sensor of the present invention comprises a lithium ionic conducting glass thin film having a dense structure, so that, even if the carbon dioxide sensor is used in the form of a thin film, it enables complete elimination of noise attributed to gas permeation, thereby realizing an improvement of accuracy in measurement of carbon dioxide concentration as well as miniaturization of the sensor.

Further, thin carbon dioxide sensor of the present invention is formed into a thin film, so that the sensor has a low internal resistance, acts at low operating temperatures and exhibits a high response speed. Therefore, a heater having a capacity smaller than in the prior art can be used in the thin carbon dioxide sensor of the present invention, so that, even when a structure integral with a heater and the like is employed, miniaturization and power saving can be attained for the integrated carbon dioxide sensor.

Moreover, the whole body of the thin carbon dioxide sensor of the present invention in which an oxide ionic conducting ceramic is used as a substrate or thin film can be inserted in a subject gas in the measurement of carbon dioxide concentration because the oxygen ionic conducting ceramic shuts off ions other than oxygen ions.

The thin carbon dioxide sensor of the present invention can find applications in various fields such as environment, agriculture and medical care.

EXAMPLES

The present invention will now be illustrated with reference to the following Examples, which in no way limit the scope of the invention.

Example 1
Production of thin carbon dioxide sensor of structure shown in FIG. 1

A reagent of lithium carbonate was weighed in a predetermined amount, put in an alumina crucible and heated in an electric furnace at about 750° C. for about 3 hr. A meshed platinum (100 mesh) as an electrode 2 was dipped in the thus molten lithium carbonate to effect coating. Thus, a layer of metal carbonate 1 having a thickness of about 0.5 mm was formed.

Subsequently, oxygen-reactive sputtering was performed on one surface of the layer of metal carbonate 1 with the use of a sintered body of $Li_2SiO_3$ as a target, thereby forming a solid electrolyte of an $(Li_2O)_{50}$—$(SiO_2)_{50}$ film 3 having a thickness of about 1 μm.

Then, a platinum sputter film of about 0.5 μm in thickness was formed as an electrode 4 on the solid electrolyte.

Thereafter, platinum leads 5 and 6 were connected to the electrode 2 composed of platinum mesh and the electrode 4 composed of platinum sputter film, respectively. Thus, a carbon dioxide sensor was obtained.

The side of metal carbonate 1 of the thus obtained sensor was exposed to a subject atmosphere whose carbon dioxide concentration changed from 500 ppm to 1% by volume while the platinum sputter film side of the sensor was exposed to the air, and the electromotive force generated between the platinum leads 5 and 6 was measured at an operating temperature of 400° C. During the measurement, the subject atmosphere and the air as the reference atmosphere was partitioned by means of a glass tube.

Figure 5:
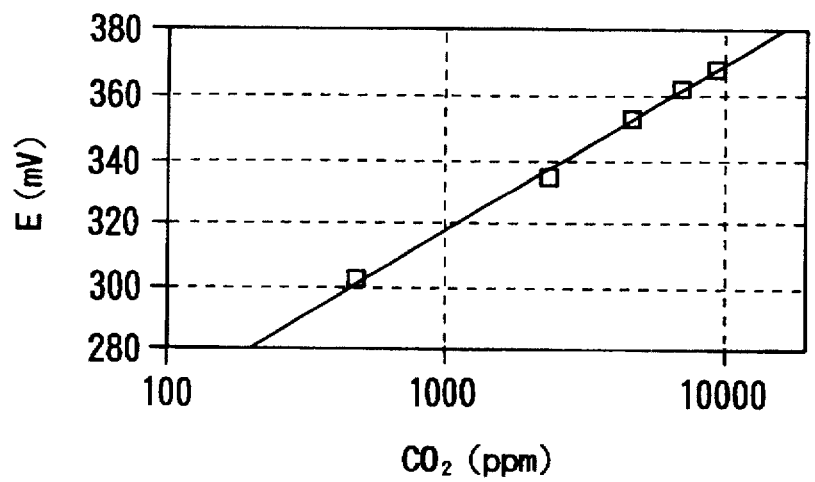
FIG. 5 is a graph showing the relationship between the electromotive force and the concentration of carbon dioxide at an operating temperature of 400° C. as measured by the use of the thin carbon dioxide sensor of Example 1 of the present invention.

The measurement results are shown in FIG. 5.

FIG. 5 demonstrates that a thin carbon dioxide sensor exhibiting a good linearity in accordance with the Nernst formula was obtained in Example 1.

Example 2
Production of thin carbon dioxide sensor of structure shown in FIG. 3

A lithium ionic conducting glass thin film 17 of about 1 μm in thickness was formed as a solid electrolyte on part of a surface of a $ZrO_2$ substrate 16 (size: 10 mm×10 mm×0.5 mm) having a $Y_2O_3$ content of 8 mol %. The lithium ionic conducting glass thin film 17 was prepared by the oxygen-reactive radio-frequency (RF) magnetron sputtering process with the use of molten lithium silicate ($Li_2SiO_3$) as a target, and its composition was regulated to $(Li_2O)_{45}$—$(SiO_2)_{55}$ by a quartz chip placed on the target. The crystallization temperature of the lithium ionic conducting glass thin film 17 is not lower than 600° C.

Subsequently, a thin lithium carbonate film of about 1 μm in thickness as a thin metal carbonate film 19 constituting a detector electrode and a thin gold film of about 0.21 μm in thickness as a thin noble metal electrode film 20 were laminated to the above lithium ionic conducting glass thin film 17. The thin lithium carbonate film was prepared by the radio-frequency magnetron sputtering process with the use of molten lithium carbonate as a target. The thin gold film was prepared by the direct-current (DC) magnetron sputtering process with the use of gold as a target.

Thereafter, a thin gold film as a thin noble metal electrode film 18 constituting a reference electrode was formed on the same side of the substrate 16 as provided with the laminate of the lithium ionic conducting glass thin film 17, the thin metal carbonate film 19 and the thin noble metal electrode film 20 with a spacing given between this thin gold film and the laminate. This thin gold film was prepared in the same manner as employed to obtain the above thin gold film as the thin noble metal electrode film 20.

A thin film heater 21 was formed on the back of the oxygen ionic conducting ceramic substrate 16, i.e., the surface of the oxygen ionic conducting ceramic substrate 16 on which the above laminate of the lithium ionic conducting glass thin film 17, the thin noble metal electrode film 18, etc. was not provided. The thin film heater 21 was a thin platinum film of 2 μm in thickness and was prepared by the direct-current (DC) magnetron sputtering process with the use of platinum as a target.

Finally, gold leads as leads 22 and 23 for electromotive force measurement were connected by ultrasonic fusion to the thin gold film as the thin noble metal electrode film 18 and the thin gold film as the thin noble metal electrode film 20, respectively. Thus, a carbon dioxide sensor was obtained.

The whole body of the thus obtained sensor was inserted in subject atmospheres of varied carbon dioxide concentrations, and the electromotive force generated between the gold lead as lead 22 for electromotive force measurement and the gold lead 23 as lead for electromotive force measurement was measured at an operating temperature of 400° C. Direct-current voltage was applied to the thin film heater 21 so as to hold the operating temperature constant at 400° C.

Figure 6:
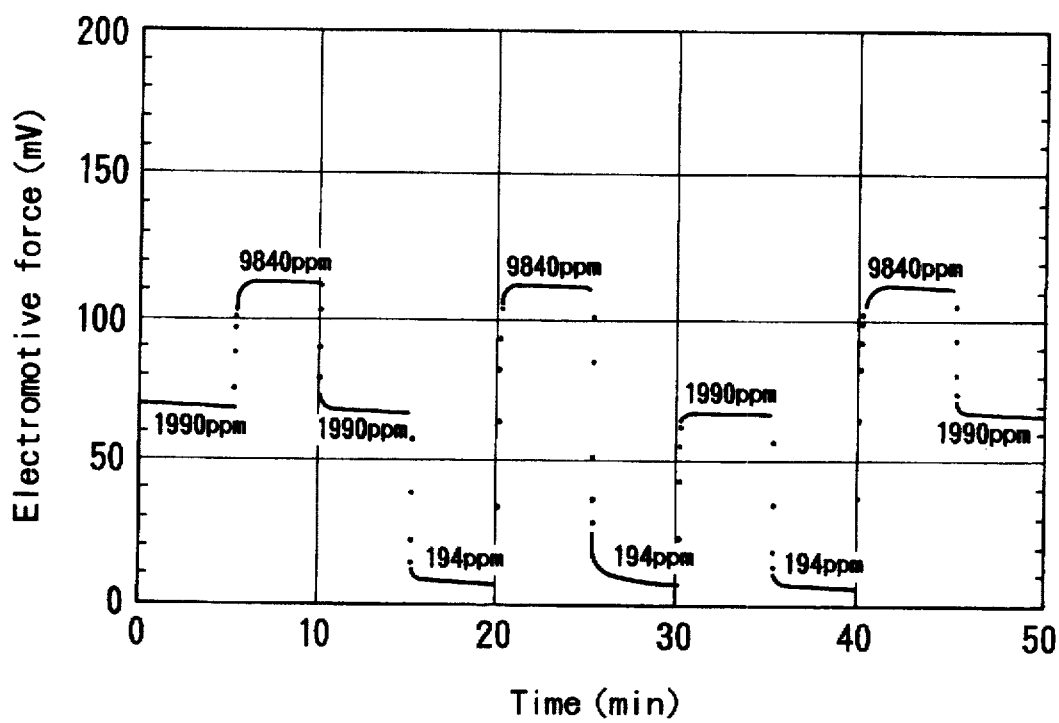
FIG. 6 is a view showing electromotive force response waveforms of the thin carbon dioxide sensor of Example 2 of the present invention to various carbon dioxide concentrations.

Measured electromotive force response waveforms to various carbon dioxide concentrations are shown in FIG. 6. The 90% response speed of electromotive force was about 10 sec at the first transition (194 ppm →9840 ppm) and about 30 sec at the last transition (9840 ppm →194 ppm). This shows a striking improvement of the 90% response speed which has inevitably been about several minutes.

Figure 7:
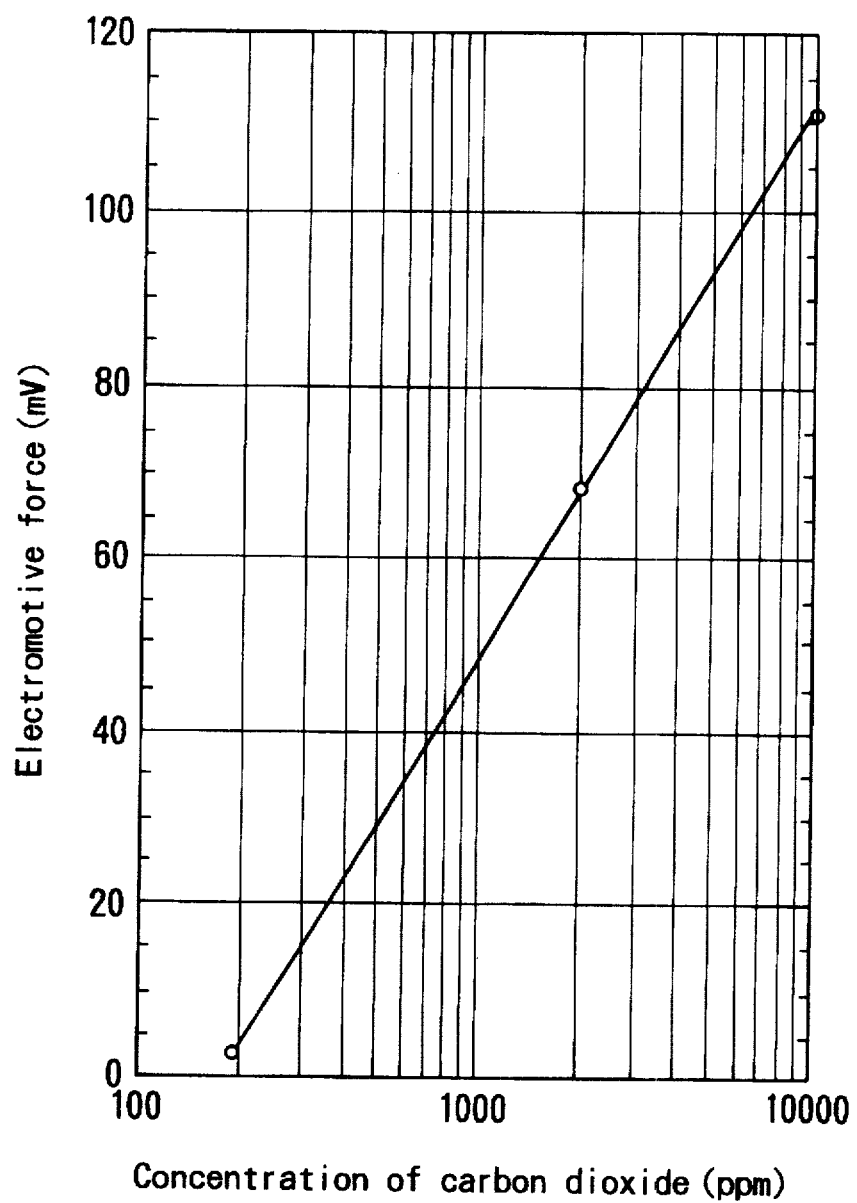
FIG. 7 is a graph showing the relationship between the electromotive force and the concentration of carbon dioxide at an operating temperature of 400° C. as measured by the use of the thin carbon dioxide sensor of Example 2 of the present invention.

Further, the relationship between measured carbon dioxide concentration and electromotive force is shown in FIG. 7. As apparent from FIG. 7, a thin carbon dioxide sensor exhibiting a good linearity in accordance with the Nernst formula was obtained in Example 2.

The same results as obtained with the thin carbon dioxide sensor of Example 2 are exhibited by the thin carbon dioxide sensors having structures shown in FIGS. 2 and 4 as well.

I claim:

1. A thin carbon dioxide sensor comprising a lithium ionic conducting glass thin film solid electrolyte with 0.1 to 20 μm thickness consisting essentially of a glass containing 20 to 80 mol % of a $Li_2O$ component and 80 to 20 mol % of a member selected from the group consisting of $SiO_2$, $P_2O_5$, $B_2O_3$ and $Al_2O_3$ and an electrode comprising a carbonate material for detecting carbon dioxide.

2. The thin carbon dioxide sensor as claimed in claim 1, wherein the lithium ionic conducting glass thin film solid electrolyte consists essentially of a material represented by the formula:

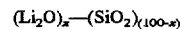

wherein 20 mol % ≧ x mol % ≧ 80 mol %.

3. The thin carbon dioxide sensor as claimed in claim 2, wherein the lithium ionic conducting glass thin film is formed by the sputtering process.

4. The thin carbon dioxide sensor as claimed in claim 1, wherein the lithium ionic conducting glass thin film and a thin metal carbonate film in this sequence are laminated to one surface of an oxygen ionic conducting ceramic substrate and further a first thin noble metal electrode film is laminated to the surface of the thin metal carbonate film, and wherein a second thin noble metal electrode film and a thin film heater are laminated to the other side of said surface of the oxygen ionic conducting ceramic substrate in a fashion such that the second thin noble metal electrode film and the thin film heater are arranged so as not to contact each other.

5. The thin carbon dioxide sensor as claimed in claim 1, wherein the lithium ionic conducting glass thin film and a first thin noble metal electrode film in this sequence are laminated to one surface of an oxygen ionic conducting ceramic substrate and further a thin metal carbonate film is laminated to the surface of the first thin noble metal electrode film, and wherein a second thin noble metal electrode film and a thin film heater are laminated to the other side of said surface of the oxygen ionic conducting ceramic substrate in a fashion such that the second thin noble metal electrode film and the thin film heater are arranged so as not to contact each other.

6. The thin carbon dioxide sensor as claimed in claim 1, wherein the lithium ionic conducting glass thin film and a first thin noble metal electrode film are laminated to one surface of an oxygen ionic conducting ceramic substrate in a fashion such that the lithium ionic conducting glass thin film and the first thin noble metal electrode film are arranged so as not to contact each other, a thin metal carbonate film is laminated to the surface of the lithium ionic conducting glass thin film and further a second thin noble metal electrode film is laminated to the surface of the thin metal carbonate film, and wherein a thin film heater is laminated to the other side of said surface of the oxygen ionic conducting ceramic substrate.

7. The thin carbon dioxide sensor as claimed in claim 1, wherein the lithium ionic conducting glass thin film and a first thin noble metal electrode film are laminated to one surface of an oxygen ionic conducting ceramic substrate in a fashion such that the lithium ionic conducting glass thin film and the first thin noble metal electrode film are arranged so as not to contact each other, a second thin noble metal electrode film is laminated to the surface of the lithium ionic conducting glass thin film and further a thin metal carbonate film is laminated to the surface of the second thin noble metal electrode film, and wherein a thin film heater is laminated to the other side of said surface of the oxygen ionic conducting ceramic substrate.

8. The thin carbon dioxide sensor as claimed in claim 1, wherein an oxygen ionic conducting ceramic thin film is laminated to a surface of a plane heater substrate, the lithium ionic conducting glass thin film and a first thin noble metal electrode film are laminated to the surface of the oxygen ionic conducting ceramic thin film in a fashion such that the lithium ionic conducting glass thin film and the first thin noble metal electrode film are arranged so as not to contact each other, a thin metal carbonate film is laminated to the surface of the lithium ionic conducting glass thin film and further a second thin noble metal electrode film is laminated to the surface of the thin metal carbonate film.

9. The thin carbon dioxide sensor as claimed in claim 1, wherein an oxygen ionic conducting ceramic thin film is laminated to a surface of a plane heater substrate, the lithium ionic conducting glass thin film and a first thin noble metal electrode film are laminated to the surface of the oxygen ionic conducting ceramic thin film in a fashion such that the lithium ionic conducting glass thin film and the first thin noble metal electrode film are arranged so as not to contact each other, a second thin noble metal electrode film is laminated to the surface of the lithium ionic conducing glass thin film and further a thin metal carbonate film is laminated to the surface of the second thin noble metal electrode film.

10. The thin carbon dioxide sensor as claimed in claim 1, wherein an oxygen ionic conducting ceramic substrate is laminated to a surface of a plane heater substrate, the lithium ionic conducting glass thin film and a first thin noble metal electrode film are laminated to the surface of the oxygen ionic conducting ceramic substrate in a fashion such that the lithium ionic conducting glass thin film and the first thin noble metal electrode film are arranged so as not to contact each other, a thin metal carbonate film is laminated to the surface of the lithium ionic conducting glass thin film and further a second thin noble metal electrode is laminated to the surface of the thin metal carbonate film.

11. The thin carbon dioxide sensor as claimed in claim 1, wherein an oxygen ionic conducting ceramic substrate is laminated to a surface of a plane heater substrate, the lithium ionic conducting glass thin film and a first thin noble metal electrode film are laminated to the surface of the oxygen ionic conducting ceramic substrate in a fashion such that the lithium ionic conducting glass thin film and the first thin noble metal electrode film are arranged so as not to contact each other, a second thin noble metal electrode film is laminated to the surface of the lithium ionic conducting glass thin film and further a thin metal carbonate film is laminated to the surface of the second thin metal electrode film.

12. The thin carbon dioxide sensor as claimed in claim 1, wherein the lithium ionic conducting glass thin film is formed on an oxygen ionic conducting ceramic substrate.

13. A thin carbon dioxide sensor comprising a lithium ionic conducting glass thin film solid electrolyte 0.1 to 20 µm thick and consisting essentially of a glass containing 20 to 80 mol % of an $LiO_2$ component and 80 to 20 mol % of a $SiO_2$ component, a detecting electrode comprising a first thin noble metal electrode film and a thin metal carbonate film and a reference electrode comprising an oxygen ionic conducting ceramic substrate and a second thin noble metal electrode film, wherein the lithium ionic conducting glass thin film solid electrolyte is disposed between the detecting electrode and the reference electrode.

14. The thin carbon dioxide sensor as claimed in claim 13, wherein the lithium ionic conducting glass thin film contains 40 to 60 mol % of a $LiO_2$ component and 60 to 40 mol % of a $SiO_2$ component.

15. The thin carbon dioxide sensor as claimed in claim 13, wherein the lithium ionic conducting glass thin film is formed by the sputtering process.

16. The thin carbon dioxide sensor as claimed in claim 13, wherein the lithium ionic conducting glass thin film and a thin metal carbonate film with 0.1 to 20 µm thickness in this sequence are laminated to one surface of an oxygen ionic conducting ceramic substrate with 20 µm to 1 mm thickness and further the first thin noble metal electrode film is laminated to the surface of the thin metal carbonate film, and wherein the second thin noble metal electrode film and a thin film heater are laminated to the other side of said surface of the oxygen ionic conducting ceramic substrate in a fashion such that the second thin noble metal electrode film and the thin film heater are arranged so as not to contact each other.

17. The thin carbon dioxide sensor as claimed in claim 13, wherein the lithium ionic conducting glass thin film and the first thin noble metal electrode film in this sequence are laminated to one surface of an oxygen ionic conducting ceramic substrate with 20 μm to 1 mm thickness and further a thin metal carbonate film with 0.1 to 20 μm thickness is laminated to the surface of the first thin noble metal electrode film, and wherein the second thin noble metal electrode film and a thin film heater are laminated to the other side of the surface of the oxygen ionic conducting ceramic substrate in a fashion such that the second thin noble metal electrode film and the thin film heater are arranged so as not to contact each other.

18. The thin carbon dioxide sensor as claimed in claim 13, wherein the lithium ionic conducting glass thin film and the second thin noble metal electrode film are laminated to one surface of an oxygen ionic conducting ceramic substrate with 20 μm to 1 mm thickness in a fashion such that the lithium ionic conducting glass thin film and the thin noble metal electrode film are arranged so as not to contact each other, a thin metal carbonate film with 0.1 to 20 μm thickness is laminated to the surface of the lithium ionic conducting glass thin film and further the first thin noble metal electrode film is laminated to the surface of the thin metal carbonate film, and wherein a thin film heater is laminated to the other side of said surface of the oxygen ionic conducting ceramic substrate.

19. The thin carbon dioxide sensor as claimed in claim 13, wherein the lithium ionic conducting glass thin film and the second thin noble metal electrode film are laminated to one surface of an oxygen ionic conducting ceramic substrate with 20 μm to 1 mm thickness in a fashion such that the lithium ionic conducting glass thin film and the second thin noble metal electrode film are arranged so as not to contact each other, the first thin noble metal electrode film is laminated to the surface of the lithium ionic conducting glass thin film and further a thin metal carbonate film with 0.1 to 20 μm thickness is laminated to the surface of the first thin noble metal electrode film, and wherein a thin film heater is laminated to the other side of said surface of the oxygen ionic conducting ceramic substrate.

20. The thin carbon dioxide sensor as claimed in claim 13, wherein an oxygen ionic conducting ceramic thin film with 0.1 to 20 μm thickness is laminated to a surface of a plane heater substrate, the lithium ionic conducting glass thin film and the second thin noble metal electrode film are laminated to the surface of the oxygen ionic conducting ceramic thin film in a fashion such that the lithium ionic conducting glass thin film and the second thin noble metal electrode film are arranged so as not to contact each other, a thin metal carbonate film with 0.1 to 20 μm thickness is laminated to the surface of the lithium ionic conducting glass thin film and further the first thin noble metal electrode film is laminated to the surface of the thin metal carbonate film.

21. The thin carbon dioxide sensor as claimed in claim 13, wherein an oxygen ionic conducting ceramic thin film with 0.1 to 20 μm thickness is laminated to a surface of a plane heater substrate, the lithium ionic conducting glass thin film and the second thin noble metal electrode film are laminated to the surface of the oxygen ionic conducting ceramic thin film in a fashion such that the lithium ionic conducting glass thin film and the second thin noble metal electrode film are arranged so as not to contact each other, the first thin noble metal electrode film is laminated to the surface of the lithium ionic conducting glass thin film and further a thin metal carbonate film with 0.1 to 20 μm thickness is laminated to the surface of the first thin noble metal electrode film.

* * * * *